(12) United States Patent
Holman et al.

(10) Patent No.: US 7,491,188 B2
(45) Date of Patent: Feb. 17, 2009

(54) REINFORCED AND DRUG-ELUTING BALLOON CATHETERS AND METHODS FOR MAKING SAME

(75) Inventors: Thomas J. Holman, Princeton, MN (US); Jan Weber, Maple Grove, MN (US); Scott Schewe, Eden Prairie, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 203 days.

(21) Appl. No.: 10/963,272

(22) Filed: Oct. 12, 2004

(65) Prior Publication Data

US 2006/0079836 A1    Apr. 13, 2006

(51) Int. Cl.
*A61M 29/00* (2006.01)
(52) U.S. Cl. .............................. 604/103.01; 604/96.01
(58) Field of Classification Search ............ 604/103.01, 604/103.02, 96.01, 99.04, 101.02, 101.03, 604/103.05–103.09, 103, 104–107
See application file for complete search history.

(56) References Cited

U.S. PATENT DOCUMENTS

| | | | | |
|---|---|---|---|---|
| 4,572,186 A * | 2/1986 | Gould et al. | ................ | 606/194 |
| 5,176,638 A | 1/1993 | Don Michael | .............. | 604/101 |
| 5,308,325 A | 5/1994 | Quinn et al. | ................... | 604/96 |
| 5,328,469 A * | 7/1994 | Coletti | ................... | 604/103.09 |
| 5,466,222 A * | 11/1995 | Ressemann et al. | .... | 604/103.09 |
| 5,470,314 A * | 11/1995 | Walinsky | ............... | 604/103.11 |
| 5,501,667 A | 3/1996 | Verduin, Jr. | ................... | 604/96 |
| 5,514,153 A | 5/1996 | Bonutti | ....................... | 606/190 |
| 5,549,552 A | 8/1996 | Peters et al. | .................. | 604/96 |
| 5,681,343 A | 10/1997 | Miller | ........................ | 606/192 |
| 6,010,511 A | 1/2000 | Murphy | ....................... | 606/108 |
| 6,315,757 B1 | 11/2001 | Chee et al. | ............. | 604/103.09 |
| 6,629,952 B1 | 10/2003 | Chien et al. | ............ | 604/103.09 |
| 2002/0041940 A1 | 4/2002 | Jung, Jr. et al. | ............ | 428/35.2 |
| 2002/0068953 A1 | 6/2002 | Kokish | ........................ | 606/194 |
| 2004/0106904 A1* | 6/2004 | Gonnelli et al. | ............. | 604/173 |
| 2004/0106987 A1 | 6/2004 | Palasis et al. | .............. | 623/1.42 |
| 2004/0162575 A1 | 8/2004 | Wu et al. | ..................... | 606/194 |

FOREIGN PATENT DOCUMENTS

| EP | 0 330 376 | 8/1989 |
|---|---|---|
| EP | 0 567 788 A1 | 11/1993 |
| EP | 567788 A1 * | 11/1993 |

* cited by examiner

*Primary Examiner*—Nicholas D. Lucchesi
*Assistant Examiner*—Theodore J Stigell
(74) *Attorney, Agent, or Firm*—Mayer & Williams PC; David B. Bonham, Esq.; Keum J. Park, Esq.

(57) ABSTRACT

The present invention generally relates to the field of intravascular medical devices, and more specifically to the field of balloon catheters and other similar diagnostic or therapeutic catheters within the body for treatment and diagnosis of diseases. In particular, the present invention relates to reinforced balloon catheters and drug-eluting balloon catheters and corresponding methods for producing same.

12 Claims, 13 Drawing Sheets

REINFORCED AND DRUG-ELUTING BALLOON CATHETERS AND METHODS FOR MAKING SAME

FIELD OF THE PRESENT INVENTION

The present invention generally relates to the field of intravascular medical devices, and more specifically to the field of balloon catheters and other similar diagnostic or therapeutic devices for insertion or implantation within the body for treatment or diagnosis of diseases.

BACKGROUND

Balloon catheters are being increasingly used to reach remote locations in the body of a patient. When the target is a soft tissue site, the vascular system in the region often consists of vessels of very small diameter. The vessels are also often convoluted, making many sharp twist and bends. To navigate these small tortuous vessels requires a catheter having a correspondingly small outside diameter. The predominant method for achieving small diameters is to use catheters having very thin walls. However, as the walls of a catheter get thinner, they tend to lose their torsional and longitudinal rigidity. Sufficient torsional rigidity must be maintained to permit steering of the catheter through the vessel and sufficient longitudinal rigidity must remain to allow the catheter to be advanced (i.e., pushed) through the vessel. Furthermore, thin wall tubes have a tendency to crimp or kink when bent in a small radius. This can result in the binding of guide wires within the catheter in the vessel which normally depends on prior advancement of a guide wire.

The problem of achieving a small tube diameter while still having sufficient torsional control and longitudinal control and kink resistance is compounded in cases where a catheter having more than one channel or tube is required, such as in the treatment of atherosclerotic lesions in the arteries of the brain, in which a balloon catheter is used that is similar to, but much smaller than, that employed for percutaneous transluminal coronary angioplasty. Such a catheter is typically composed of two tubes, an outer tube that, at or near its distal end, is in fluid communication with a balloon-like structure and an inner tube through which a guide wire or other instrumentation may be passed. The annular space between the two tubes provides a channel through which liquids can be introduced and removed to inflate and deflate the balloon.

The general approach to accommodating the need for small outside diameter catheters is to reduce the size of guide wires and the wall thickness of both tubes making up a balloon catheter. However, there are limits to the extent to which these dimensional reductions can be taken. If the diameter of the guide wire is reduced too much, the guide wire will lose its ability to effectively transmit torsional and axial (i.e., longitudinal) forces necessary to steer and advance the guide wire through tortuous vascular systems. Thus, if the diameter of the wire is to be maintained at a functional dimension, then the first impulse is to reduce overall catheter size by reducing the wall thickness of the tubular portions of the catheters.

Unfortunately, this can result in loss of cross-sectional circularity of either or both the inside and outside tubes, resulting in crimping or kinking. If the inner tube kinks, then the guide wire will become bound within the tube's lumen and can no longer be advanced through the vascular system. If the outer tube kinks, it may cause the inner tube to close down and bind the guide wire or it may constrict, even close down, the annular space between the tubes making it difficult or impossible to expand and deflate the balloon structure.

Thus, there is a need for a balloon catheter structure combining a thin overall cross-section with controlled flexibility, kink resistance and the structural strength to withstand the high pressures created during the inflation of the balloon portion of the catheter.

SUMMARY OF THE PRESENT INVENTION

The present invention addresses these and other needs by providing reinforced balloon catheters and drug-eluting balloon catheters having a desired combination of strength and flexibility and/or the ability to provide therapeutic agents in vivo.

According to a first aspect of the present invention, a balloon catheter device is provided which comprises an inflatable balloon having an inner surface that defines an inner volume, and an elongate member having an outer surface. The elongate member is disposed within the inner volume of the inflatable balloon such that a lumen is established between the inner surface of the balloon and the outer surface of the elongate member when the balloon is in a non-collapsed state. In addition, a plurality of strands traverse portions of the lumen. For example, at least some of the strands can be disposed between the inner surface of the balloon and the outer surface of the elongate member. As another example, at least some of the strands can be disposed between a first location on the inner surface of the balloon and a second location on the inner surface of the balloon. As yet another example, at least some of the strands correspond to regions between slits in an elastic tube.

According to another aspect of the inventing a therapeutic medical article is provided which comprises an inflatable balloon having a an inner surface that defines a inner volume and an elongate member having an outer surface, which is disposed within the inner volume of the inflatable balloon such that a lumen is established between the inner surface of the balloon and the outer surface of the elongate member when the balloon is in a non-collapsed state. A plurality of flexible hollow members are disposed in the lumen. Each hollow member comprises an exterior surface and an interior cavity containing a therapeutic agent, with a portion of the exterior surface being attached to the inner surface of the balloon. Each hollow member also has an associated channel that extends (a) from the outer surface of the balloon to the interior cavity of the hollow member or (b) from the outer surface of the balloon to a puncturing member, disposed between inner surface of the balloon and the exterior surface of the hollow member, which punctures the hollow member upon inflation of the balloon. In either case, the device is adapted such that therapeutic agent contained in the interior cavity of the hollow member exits the device through the channel upon inflation of the balloon.

According to another aspect of the present invention, a method of manufacturing a reinforced balloon catheter is provided which comprises the following steps: First, a catheter assembly is provided that comprises an elongate member having a plurality of strands attached to its outer surface. The elongate member is disposed within an inner volume of a balloon that has an adhesive material disposed on its inner surface, such that a lumen is formed between the outer surface of the elongate member and the inner surface of the balloon when the balloon is in a non-collapsed state. Subsequently, a force is produced that urges at least some of the strands into contact with the adhesive material disposed on the inner surface of the balloon, such that upon cure of said adhesive material and upon inflation of the balloon, a plurality of strands that traverse portions of the lumen between the elongate member and the balloon. Examples of forces include centrifugal and electrostatic forces.

These and other aspects, along with various advantages and features of the present invention, will become apparent through reference to the following description, the accompanying drawings, and the claims. Furthermore, it is to be understood that the features of the various embodiments described herein are not mutually exclusive and can exist in various combinations and permutations.

BRIEF DESCRIPTION OF THE DRAWINGS

FIG. 1A is a schematic illustration of some of the major steps for producing the catheter wherein ends of strands, e.g., reinforcing fibers, are attached to the outer surface of an inner shaft of a balloon catheter, which is placed within a balloon and the resulting assembly rotated around its longitudinal axis. This results in radial attachment of the fibers from the inner surface of the outer tube to the outer surface of the inner shaft. FIG. 1B shows a cross-section of the resulting catheter assembly of FIG. 1A along line A-A.

FIG. 2A schematic illustrates an inner shaft of a fiber-reinforced balloon catheter. As shown, both ends of two representative reinforcing fibers are attached to the outer surface of the inner shaft. FIG. 2B is a see-through view of a fiber-reinforced balloon catheter assembled from the reinforced inner shaft illustrated in FIG. 2A.

FIG. 4B schematically illustrates a manufacturing assembly for producing balloons having a plurality of lobes. FIG. 4C is a schematic illustration of a cross-section of the assembly of FIG. 4B along line A-A.

FIG. 5A is a see-through view of one embodiment of a drug-eluting balloon catheter having hollow sac-like structures that are attached to the inner surface of the balloon and to the outer surface of the inner shaft. FIG. 5B schematically illustrates a close-up of a longitudinal section of the catheter of FIG. 5A, wherein an opening is made through the balloon wall and into the lumen of the sac-like structure and a therapeutic substance is inserted into the hollow structure through the opening. FIG. 5C schematically illustrates another close-up of a longitudinal-sectional view of the catheter, showing the release of the therapeutic agent from the hollow structures. Inflation of the balloon results in increase in internal pressure within the balloon that causes the therapeutic agent to be squeezed out of the hollow structure and the balloon catheter and onto/into the adjoining lumen wall.

FIG. 6A is a see-through view of one embodiment of a drug-eluting balloon catheter in which sacs are adhered directly to the inner surface of the balloon wall. FIG. 6B schematically illustrates a longitudinal-sectional view of the catheter, showing the release of the therapeutic agent from the sac. FIG. 6C schematically illustrates a longitudinal-sectional view of a drug-eluting balloon catheter wherein a needle is disposed between the hollow structure and the balloon wall.

FIG. 9A is a schematic illustration of an assembly comprising a coated pin with a plurality of attached fibers. FIG. 9B is a schematic see-though illustration of an assembly comprising the assembly of FIG. 9A subsequent to insertion into an adhesive coated balloon. FIG. 9C is a schematic see-through view of a fiber-reinforced balloon assembled from the assembly of FIG. 9B.

DETAILED DESCRIPTION

A more complete understanding of the methods and apparatuses of the present invention are available by reference to the following detailed description of the embodiments when taken in conjunction with the accompanying drawings. The detailed description of the embodiments which follows is intended to illustrate but not limit the present invention. The scope of the present invention is defined by the appended claims.

Figure 1A:
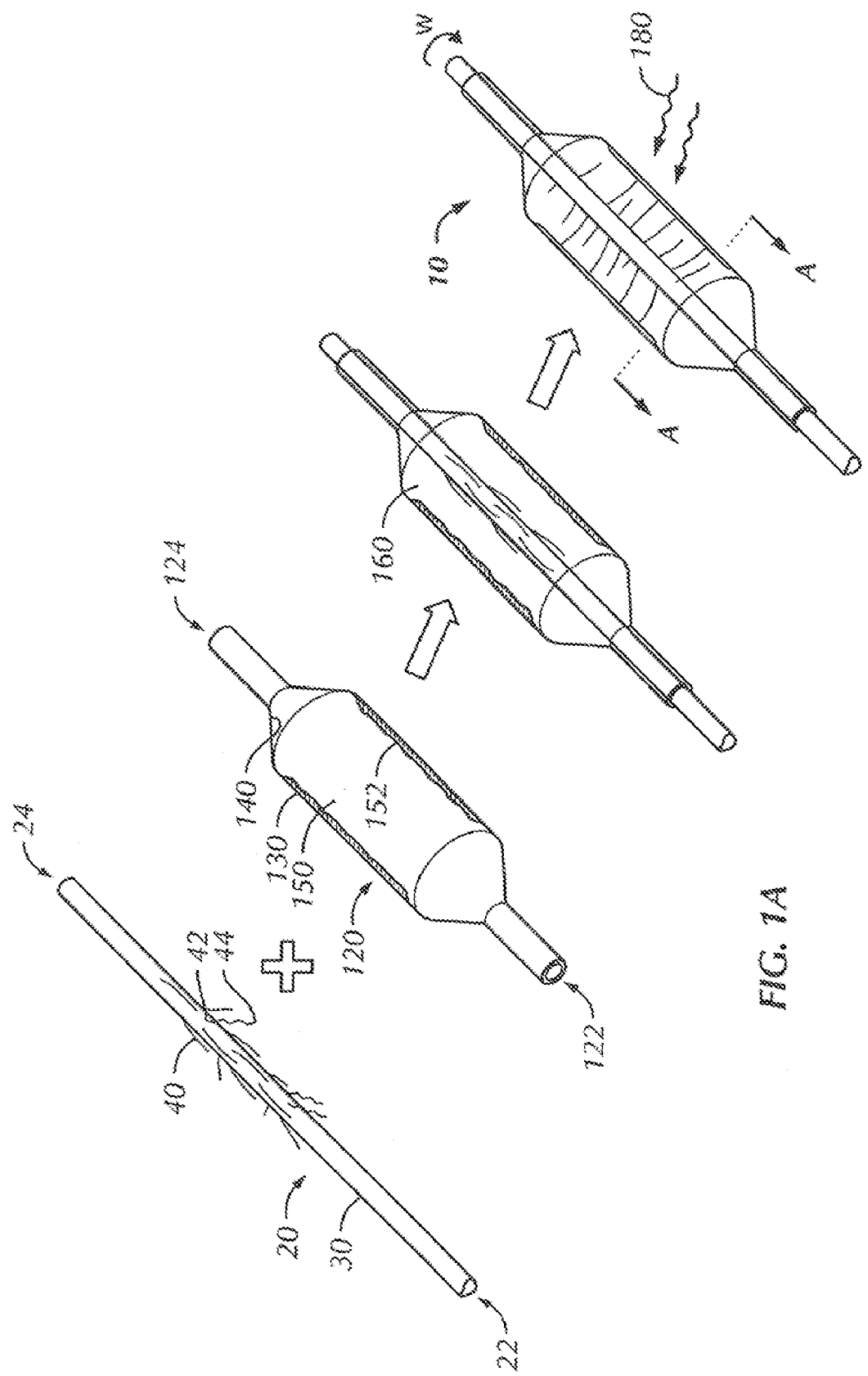
FIGS. 1A and 1B are schematic illustrations of a fiber-reinforced balloon catheter according to an embodiment of the present invention.

FIG. 1A illustrates a method producing a reinforced balloon catheter 10, according to one particular embodiment of the present invention. The balloon catheter 10 shown comprises two components, an inflatable balloon 120 and a flexible elongate member 20. The inflatable balloon 120 comprises a proximal end 122 and a distal end 124, as well as an outer surface 130 and an inner surface 140 that defines a volume 150. The flexible elongate member 20 likewise comprises a proximal end 22 and a distal end 24 and is placed within the inner volume 150 of the inflatable balloon 120. An adhesive material 152 is applied to the inner surface 140 of the balloon 120. The elongate member 20 extends distally beyond the distal end 124 of the balloon 120 in the embodiment shown, and has an inner surface defining a cylindrical lumen and an outer surface 30 defining an outer diameter that is less than an inner diameter of the balloon, such that another lumen 160 (annular in cross-section) is formed between the balloon 120 and the elongate member 20.

Structural integrity of the balloon 120, which is subjected to high pressures during inflation, is enhanced by incorporating a plurality of reinforcing strands 40 between the inside surface of the balloon 120 and the outer surface 30 of the elongate member 20. Where the reinforcing strands 40 are elastic in nature, ease of deflation is also enhanced by the elastic rebound of the strands 40.

As shown in FIG. 1A, the plurality of reinforcing strands 40 can be attached to the outer surface 30 of the elongate member 20, which is then placed within the balloon 120. Individual strands 40, each having a first end 42 and a second end 44, as used herein, may have a variety of different geometric configurations, and typically include: (a) thin, string-like shapes of whose length is large compared to their cross-sectional dimensions (which strands can have various solid cross-sections, including circular, oval, polygonal, unshaped, etc.), (b) ribbon-like structures where each strand has a cross-sectional width and thickness and where the width is greater than the thickness, (c) a tapered configuration wherein the first end of the strand has a cross-sectional circumference and/or area that is different from that of the second end, (d) helical or coiled configurations which render the strands flexible or elastic in the longitudinal direction, (e) hollow strands whose length is large compared to their outer diameters (e.g., tubular strands whose walls define an enclosed volume of circular cross-section, triangular cross-section, rectangular cross-section, and so forth).

Strands 40 may be constructed of a variety of different materials. They may be organic or inorganic. They may be formed from a single material or multiple materials; for example, they may be formed from a blend of materials (e.g., polymer blend, metal alloy, etc.), or they have a composite or laminate construction. They may be constructed of materials that are the same as or are different from the materials used to form the balloon 120 and/or elongate material 120.

Examples of organic materials for use in strands 40 include polymeric materials comprising one or more polymers. The polymers can be elastic or inelastic. They can be cyclic, linear, or branched. Branched configurations include star-shaped configurations (e.g., configurations in which three or more chains emanate from a single branch point), comb configurations (e.g., configurations having a main chain and a plurality of side chains), dendritic configurations (e.g., arborescent and hyperbranched polymers). They can be homopolymers or copolymers (e.g., random, statistical, gradient, and periodic copolymers such as alternating copolymers.)

Specific examples of polymeric materials include the following: aromatic polyamides, also called aramids (e.g., KEVLAR), polyolefins such as polyethylene, (e.g., SPECTRA and DYNEEMA ultra-high molecular weight polyethylenes), poly(p-phenylenebenzobisthiazoles) such as TERLON, poly (p-phenylene-2,6-benzobisoxazoles) such as ZYLON, various polyimides, polyamides (nylons), silicones, polyesters such as polyethylene terephthalate or polybutylene terephthalate, polyurethanes, polyether block co-polymers such as polyether block amides, various strand-forming adhesives, liquid crystal polymers such as VECTRAN, and so forth. These strand materials are readily available commercially.

Many of the above polymers will undergo deformation and subsequent work hardening (which strengthens the polymer), once a certain degree of strain is applied, for example, due to inflation of the balloon. Hence, in some embodiments, the strands do not achieve full strength until the balloon is fully inflated within the subject.

Examples of inorganic materials for forming the strands 40 include both metallic and non-metallic inorganic materials. Specific examples of metallic materials include, for example, metals such as palladium, platinum, rhodium, tantalum and the like, as well as metal alloys such as iron-chromium alloys (e.g., stainless steels, which contain at least 50% iron and at least 11.5% chromium), cobalt-chromium alloys, nickel-titanium alloys (e.g., nitinol), cobalt-chromium-iron alloys (e.g., elgiloy alloys), and nickel-chromium alloys (e.g., inconel alloys), among many others, some of which have elastic properties. When individual strands 40 are metallic or alloy, each strand 40 has a mimimal cross-sectional dimension (e.g., diameter for a cylindrical strand, thickness for an elongated strip, wall thickness for a tubular strand, and so forth) which may vary widely, but is commonly from about 0.0004 inches to about 0.00075 inches.

Examples of non-metallic inorganic materials include ceramic and non-ceramic materials. Specific examples of non-metallic inorganic materials include carbon fibers, glass fibers and basalt fibers, among many others.

As will be appreciated by one of skill in the art, a wide variety of materials may also be used to make the balloons 120 and elongate members 20 of the present invention, including, for example, polytetrafluoroethylenes (Teflon®), polyethylenes, particularly high density polyethylenes, polypropylenes, polyurethanes, nylons including nylon 6 and nylon 12, polyesters including polyalkylene terephthalate polymers and copolymers, (e.g., thermoplastic polyester elastomers such as Hytrel®, which is a block copolymer containing a hard polybutylene terephthalate segment and soft amorphous segments based on long-chain polyether glycols), polyimides, polyamides including polyether-block-co-polyamide polymers (e.g., Pebax®), and the like. These materials may also be blended or provided in a composite or multi-layer construction. Presently polymers for use in manufacture of the various aspects of this invention are Pebax®, nylon 12 and polyethylene terephthalate for the balloon 120 and Pebax®, nylon 12, high density polyethylene (HDPE) and polyethylene terephthalate for elongate member 20.

Hence, the strands 40, the balloon 120, and the elongate member 20 may be constructed of the same or of different materials.

These and other variations in shapes, sizes and materials of the strands, balloon and elongate member are within the scope of the present invention.

As noted above, the elongate member 20 with the attached strands, when placed within the balloon 120, forms an assembly having a lumen 160 between the inner surface of the balloon and the outer surface of the elongate member 20. In one embodiment, the assembly is placed on a mandrel for support and rotated around its longitudinal axis, for example, in direction ω as illustrated (or in the opposite direction, if desired), resulting in radial attachment of the strands 40 from the outer surface 30 of the elongate member 20 to the adhesive material 152 disposed on the inner surface 140 of the balloon 120. That is, and without wishing to be bound by theory, rotation of the assembly results in centrifugal forces which cause loose ends and/or portions of the strands not already attached to the outer surface 30 of the elongate member 20 to extend in a radially-outward direction within the annular lumen, thereby forming a network of strands 40 that transverse the annular lumen 160 and reinforce the inner surface of the balloon 120.

Figure 8A:
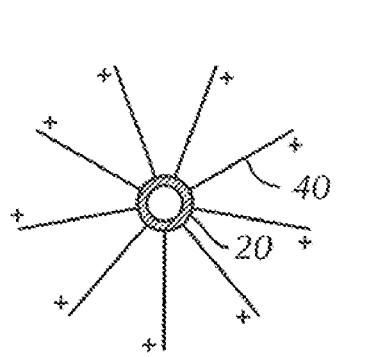
FIGS. 8A and 8B are schematic partial cross-sectional view illustrating the use of electrostatic force to radially extend strands, e.g., reinforcing fibers, in accordance with the present invention.
Figure 8B:
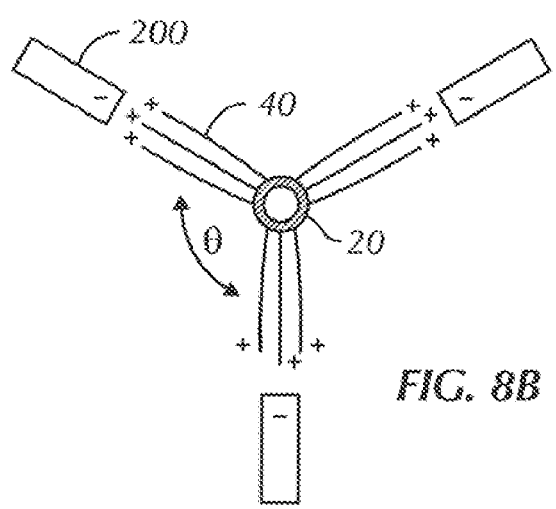

The strands can also be urged in a radially-outward direction using forces other than centrifugal forces. For instance, the strands can be urged outward using electrostatic forces. This can be done, for example, by connecting the flexible elongate member to a so-called "van de Graaf" generator. In general, the elongate member in this embodiment should be sufficiently conductive, and the fibers should be sufficiently non-conductive, to achieve the desired outward electrostatic force. Referring now to the partial (i.e., the balloon is not illustrated) schematic cross-sectional illustration of FIG. 8A, this would allow the strands 40 to unfurl from the elongate member 20 in a tangential direction, as is also the case with rotation of the elongate member 20. Moreover, as seen from the schematic partial cross-sectional illustration of FIG. 8B, by using external counter electrodes 200 of opposite charge, one can direct the loose ends of the strands 40 to certain regions. For in instance, in case where it is desired to form a three-lobed balloon, one can direct the strands to three regions separated by approximately 120 degrees of angular rotation θ as illustrated in FIG. 8B.

Referring again to FIG. 1A, an adhesive bond is created between the strands 40 and the inner surface of the balloon 120 upon cure of the adhesive material 152, for example, by application of a curing step 180, such as irradiation.

Figure 1B:
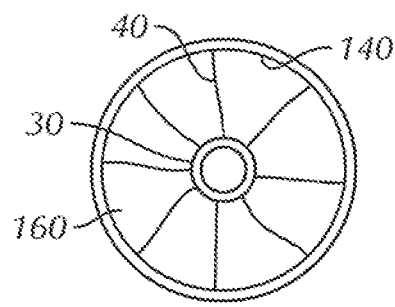

FIG. 1B shows a cross-section of one embodiment of the balloon catheter 10 of FIG. 1A along line A-A. Strands 40, in this case reinforcing fibers, are shown connected between the outer surface 30 of the elongate member and the inner surface 140 of the balloon and traverse the annular lumen 160 in a radial (e.g., "bicycle spokes") fashion. This network of strands transmits force in an inward radial direction during inflation of the balloon to support proper inflation and also during deflation of the balloon, where the strands have significant elasticity, facilitating quick return of the balloon catheter to a collapsed form.

Figure 2A:
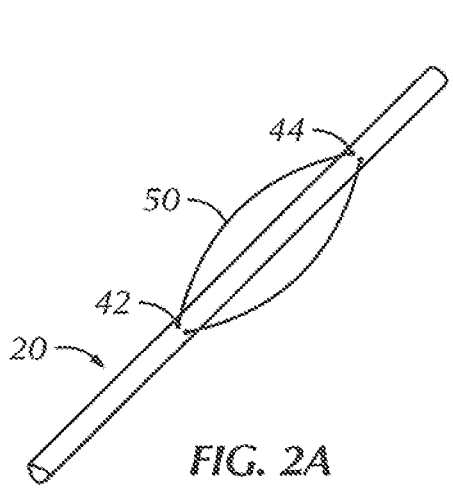
FIGS. 2A and 2B are schematic illustrations of another embodiment of a fiber-reinforced balloon catheter of the present invention.
Figure 2B:
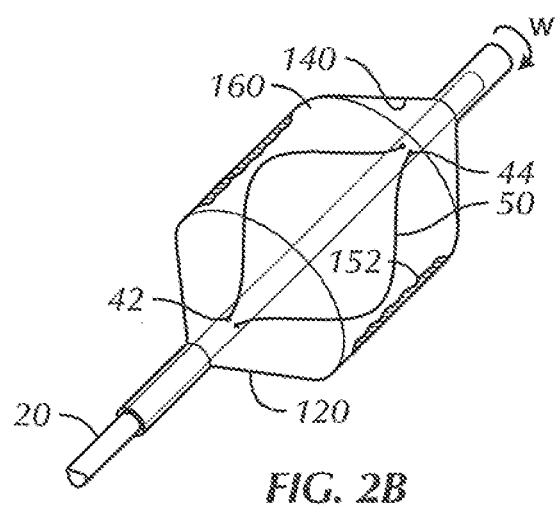

FIGS. 2A and 2B illustrate a method of manufacturing a fiber-reinforced balloon catheter in accordance with another embodiment of the present invention. As shown in FIG. 2A, in this embodiment, both ends of each strand are attached to the outer surface of the elongate member 20 to form a loop 50. The elongate member 20 with the strand 40 having both its first end 42 and second end 44 attached to the outer surface of the elongate member 20, when placed within the balloon, forms an assembly having an annular lumen 160. As discussed above, rotation of the assembly around its longitudinal axis in direction ω as indicated by FIG. 2B or the opposite direction (or the creation of electrostatic charges), results in attachment of a portion of the strand, situated between the first and second ends, to the adhesive material 152 disposed on the inner surface 140 of the balloon 120.

Figure 3:
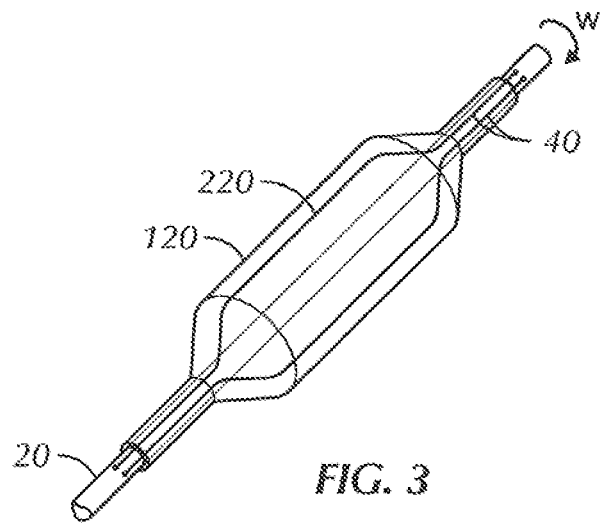
FIG. 3 is a schematic representation of a fiber-reinforced balloon catheter according to yet another embodiment of the present invention. As shown in the see-through view, a network of long fibers have adhered themselves throughout the inner surface of the balloon to form a longitudinally reinforcing layer.

As illustrated in the see-through view of FIG. 3, in one particular embodiment, the strands 40 are of sufficient length such that a large majority of the length of the strands situated between the first and second ends becomes attached to the inner surface of the balloon 120. The network of long fibers have adhered themselves along the entire length of the inner surface of the balloon 120 to form a longitudinally reinforced layer 220.

Any adhesive material capable of adhering the chosen strand material to the inner surface of the balloon (and the outer surface of the elongate member, if appropriate) may be employed in the practice of the present invention. Adhesive materials can be selected, for example, from alkyl cyanoacrylates, acrylics, esters, silicones, and polyurethanes, which may be cured by any of a number of curing mechanisms including exposure to heat, moisture, or radiation (e.g., visible, infrared, UV, RF or microwave radiation). For attachment of the strand material to the inner surface of the balloon, the curing may be performed following, or simultaneous with, the step of radially extending the strands (e.g., by rotation, electrostatic force, etc). In certain beneficial embodiments, the balloon comprises a radiation (e.g. infrared or ultraviolet) penetrable material and the adhesive material comprises a radiation curable material.

Figure 4A:
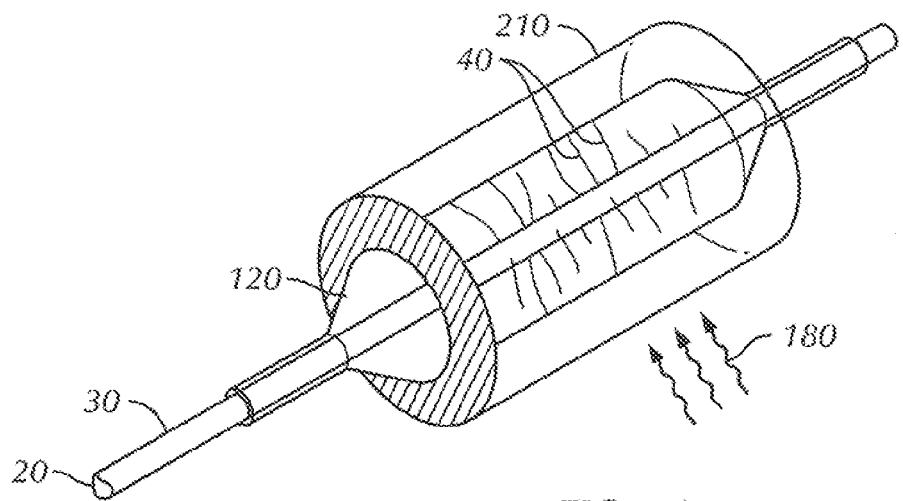
FIG. 4A is a schematic representation of a manufacturing assembly for producing balloon catheters by rotation within a light/radiation penetrable housing and curing with the application of curing radiation such as infrared or UV radiation.

Optionally, as shown in FIG. 4A, the assembly is placed in a housing 210 to temporarily contain the assembly during the rotation and curing steps. In some embodiments, the housing 210 is equipped (e.g., by including a heating or lighting element) to assist with curing of the adhesive material. In some embodiments, the housing 120 is formed of a material that allows penetration of radiation, which cures the adhesive material. An example of such material is a glass housing made out of ZnSe, which allows IR radiation to penetrate.

Although a smooth balloon with a circular cross section is used above, the present invention is applicable to wide variety of balloon types (including cutting balloons, see, e.g., U.S. Pat. No. 5,616,149, perfusion balloons, etc.), which have a variety of sizes and shapes.

Figure 4B:
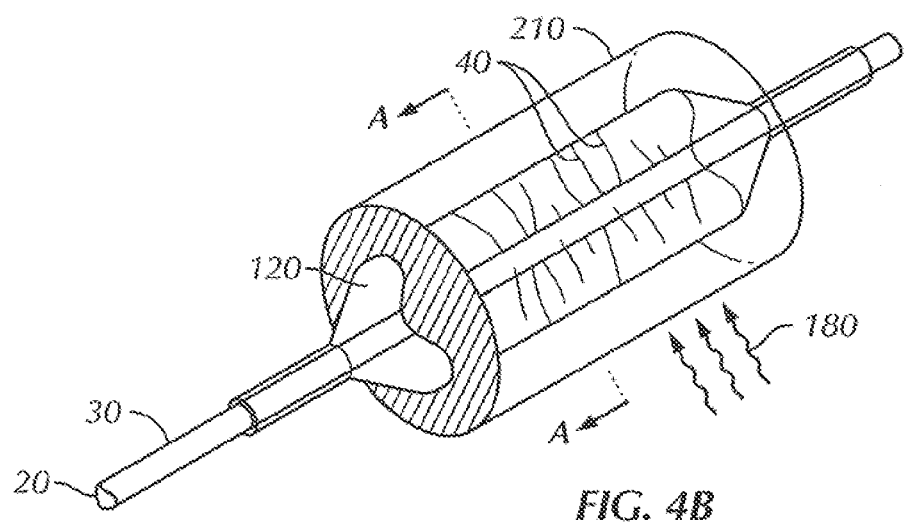
FIGS. 4B and 4C are schematic illustrations of a manufacturing assembly for producing catheters with non-circular balloons.
Figure 4C:
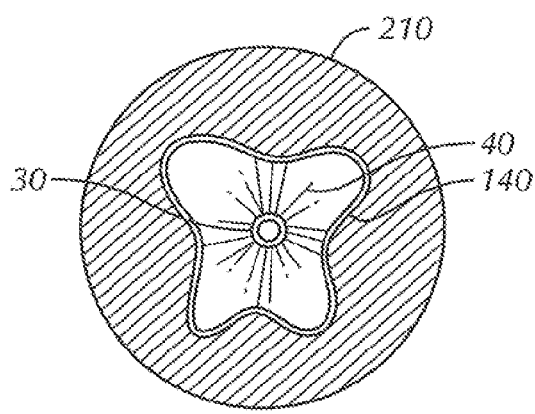

The present invention can also be used to construct balloons which inflate to non-circular cross-sections. For example, FIGS. 4B and 4C are schematic illustrations in which a non-circular balloon catheter is created according to the methods of the present invention. FIGS. 4B and 4C schematically illustrate an assembly for producing balloon catheters having a plurality of lobes. Strands 40 of differing lengths are attached to the outer surface 30 of elongate member 20 and the elongate member 20 is placed within the balloon 120. Strands 40 may be attached, for example, using an adhesive material such as described above or they may be laser bonded to the elongate member 20. The assembly is then placed inside a housing 210 or other mold having a non-circular cross-section, for example, in order to produce perfusion or other balloons, where multi-lobed or other non-circular balloon cross-sections are desired upon inflation of the balloon. FIG. 4B illustrates a cross-section of the catheter assembly of FIG. 4A along line A-A. This cross-sectional view reveals a four-lobed cross-sectional interior cavity of the housing 210. Once placed in the housing 210, the assembly is, for example, rotated around its longitudinal axis (or a charge is applied) as above, forcing the loose ends of the strands 40 in a radial outward direction. Once the strands 40 contact the adhesive material within the balloon, curing radiation 180 is applied. Strands 40, whose lengths are greater than the distance between the outer surface of the elongate member 20 and the inner surface of the balloon 120, are attached to the balloon surface. Strands whose lengths are less than that distance, on the other hand, do not contact the inner surface 140 of the balloon 120, and thus do not become attached to the balloon 120 as illustrated in FIG. 4C. Consequently, the balloon 120 is non-uniformly reinforced by the strands.

Moreover, even where strands 40 are used that are sufficiently long to contact the complete interior of balloon 140, one would still create a lobed balloon. In particular, the free length of the fibers 40 between the inner surface 140 of the balloon 120 and the outer surface 30 of elongate member 20 inner tube are longer in the lobed sections than the sections between the lobes.

When the balloon is inflated, the fact that the balloon's inner surface has reinforced and non-reinforced portions results in non-circular cross-sections, e.g., a perfusion catheter having multiple lobes. Using elastic strands will also assist with balloon folding upon deflation. The placement and length of the strands can be adapted and adjusted to produce any number of desired shapes, and according to the intended use, all of which are within the scope of the present invention.

For example, elastic or substantially inelastic strands can be employed with are sufficiently long to reach the balloon at all radial positions. This can also provide inflated balloons with non-circular cross-sections, where a non-circular housing like that employed in FIGS. 4B and 4C is employed.

Figure 4D:
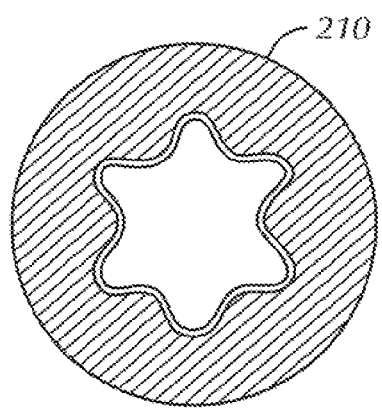
FIGS. 4D and 4E are schematic cross-sectional illustrations of additional housings for use in accordance with the present invention.
Figure 4E:
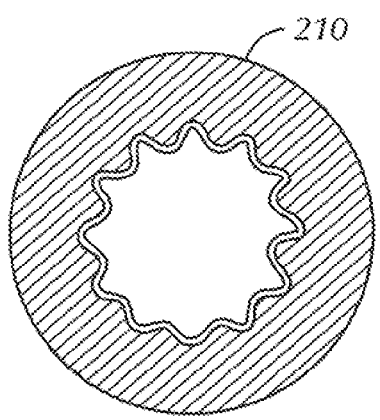

Further schematic cross-sectional illustrations of housings 210, analogous to that of FIG. 4C, are presented in FIGS. 4D and 4E, in accordance with further embodiments of the present invention.

Figure 9A:
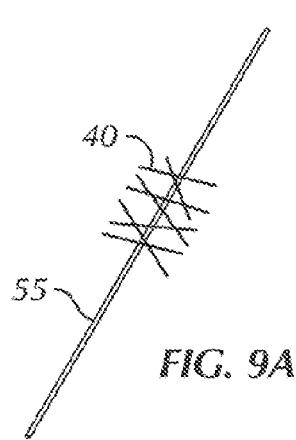
FIGS. 9A to 9C are schematic illustrations of another embodiment of a fiber-reinforced balloon in accordance with the present invention.
Figure 9B:
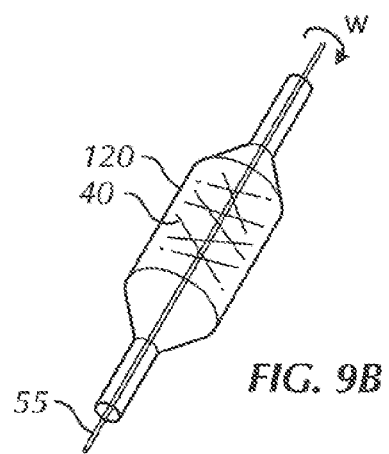
Figure 9C:
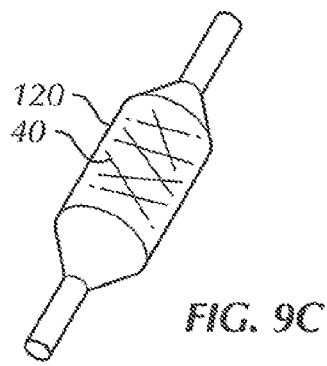

Another aspect of the present invention, in which strands are attached at both ends to the balloon, is illustrated schematically in FIGS. 9A-9C. Referring now to FIG. 9A, strands 40 are mounted in a releasable fashion to a elongate member 55. For example, each strand 40 can be attached at or near its center to a sacrificial coating on a metal pin. The strands 40 are chosen to be as long as the diameter of the balloon or longer. The elongate member 55 with attached strands 40 is then inserted into the balloon 120 as illustrated in FIG. 9B, and the strands 40 are adhered to an inner wall of the balloon 120 using techniques like those discussed above. For example, in the case of flaccid strands, forces such as centrifugal and/or electrostatic forces can be used to engage the strands 40 with the inner surface of the balloon wall, which is covered with an adhesive material, followed by cure of the adhesive material. The elongate member 55 is then removed as shown in FIG. 9C, for instance, by dissolving a sacrificial coating (e.g., a sugar layer) through which the strands were attached by to a core pin. An inner catheter tube (not illustrated) is then inserted into the balloon (e.g., using a sharp tipped object such as a needle or a cone to part the strands running through the center of the balloon) and secured. There is no need to attach the inner catheter tube to the strands in this embodiment.

In addition to providing desirable mechanical properties, the strands can also be used to measure the degree of extension of the balloon. For example, radial displacement can be converted into electric signals by using a suitable electrically active sensor material, which generates an electric charge when mechanically deformed, for instance, an electroactive polymer, a piezoelectric material, an electrostrictive material, or a material which involve Maxwell stresses. Such sensors may be structures comprising composite materials or they may include layers of different materials (e.g., metal-insulator-metal structures and innumerable other combinations). A few specific examples of electro active materials include electroactive polymers such as polypyrroles, polyanilines, polythiophenes, polyethylenedioxythiophenes, poly(p-phenylene vinylene)s, polysulfones and polyacetylenes, piezoelectric materials including ceramic materials such as Lead Zirkonate Titanate PZT-5, Lead Titanate PT, Lead Metaniobate $PbNb_2O_6$, barium titanate and quartz, metallic piezoelectric materials, additional polymer materials such as polyvinylidene fluoride (PVDF) and its copolymers with trifluoroethylene and tetrafluoroethylene, nylons with an odd number of carbons (e.g., PA 7), polyvinylchloride (PVC), polyphenylethernitrile (PPEN) and polyacrylonitrle (PAN), among many others, as well as combinations thereof.

Figure 10:
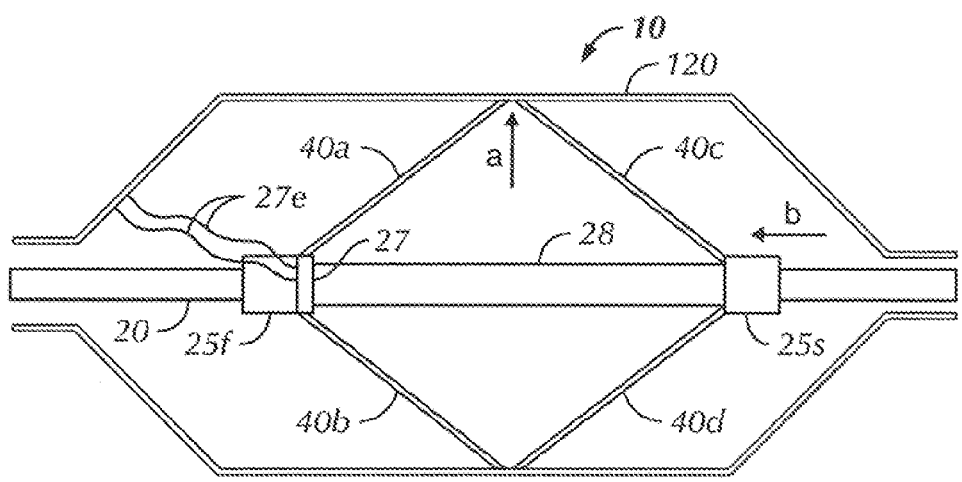
FIG. 10 is a schematic partial cross-sectional view illustrating an embodiment of a balloon catheter in accordance with the present invention by which the degree of inflation of the balloon can be measured.

A specific embodiment of this aspect of the present invention is schematically illustrated in FIG. 10. Referring now to this figure, a balloon catheter 10 is shown, which includes a balloon 120, a flexible elongate member 20 (e.g., a catheter tube), a fixed ring 25f, which is attached to the flexible elongate member 20 (and can correspond to a first marker band), a slidable ring 25s, which is slidable along a portion of the axial length of the flexible elongate member 20 (and can correspond to a second marker band), substantially inelastic strands 40a, 40b, connecting the balloon 120 to the fixed ring 25f, substantially inelastic strands 40c, 40d, connecting the balloon 120 to the slidable ring 25s, electrically active material 27, which generates an electrical signal when mechanically deformed and which is provided with electrical leads 27e, and an axially compressible and expandable member 28, which is disposed over the flexible elongate member 20 (e.g., a spring, an elastomeric tube, or another axially compressible member).

As the balloon 120 expands radially outward during operation (as shown by arrow a in FIG. 10), the slidable ring 25s moves to the left as indicated by arrow b, compressing the axially compressible member 28. This exerts stress upon the electrically active material 27, which in turn generates an electrical signal that is transmitted outside the patient via electrical leads 27e (or using another method of transmission such as a wireless transmitter) to a measurement device, which signal can be correlated to the degree of inflation of the balloon 120. (Note that strands 40a and 40b, while providing symmetry, are not needed to generate an electrical signal in this particular embodiment.)

In other embodiments, the strands 40 in various designs of the present invention are formed from a variety of actuatable materials including electrically active materials such as those described above, which mechanically deform upon application of an electrical potential, as well as shape memory alloys, which are actuated by heating and cooling (e.g., by using a heated or cooled fluid, by electrical resistance, by inductive heating, and so forth). This arrangement would allow the distension of the balloon to be fined tuned by actuating the strands, thereby making them shorter, longer or both, as desired. Specific examples of shape memory alloys include nickel-titanium alloys (nitinol), for instance, FLEXINOL fibers, which are formed of nitinol and available from Dynalloy, Inc., Costa Mesa, Calif., USA.

Figure 11A:
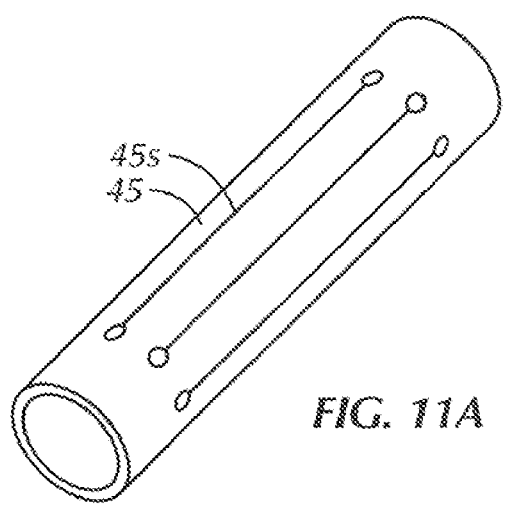
FIGS. 11A and 11B are schematic perspective views of a slotted elastic tube in resting and axially compressed configurations, respectively, according to the present invention.
Figure 11B:
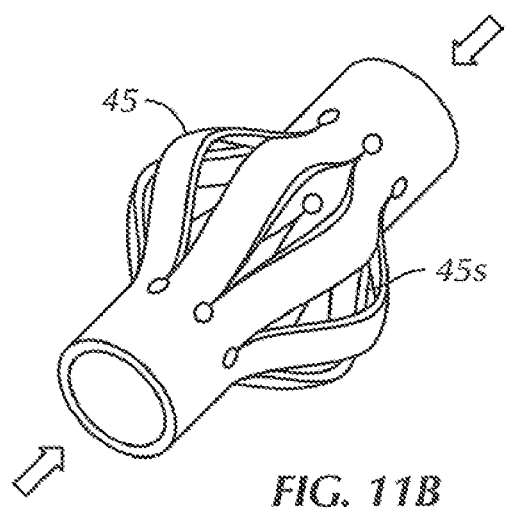
Figure 12:
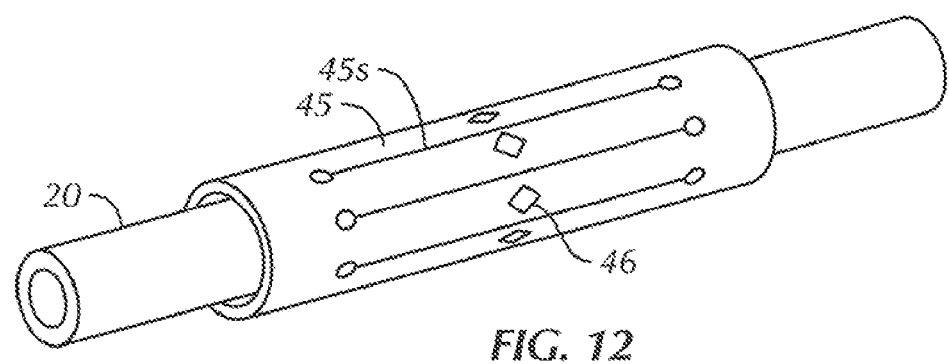
FIG. 12 is a schematic perspective view of an assembly comprising the slotted elastic tube of FIG. 11A disposed over a flexible elongate member, in accordance with the present invention.

Yet another aspect of the present invention, which is somewhat analogous to the embodiment of the present invention illustrated in FIGS. 2A and 2B, will now be described with reference to FIGS. 11A, 11B, 12 and 13. Referring to FIG. 12, an assembly is shown which includes a flexible elongate member 20 over which is disposed a tube of elastic material 45, having slits 45s. The nature of the tube of elastic material 45 can perhaps be better seen with reference to FIGS. 11A and 11B. In its normal resting state, the tube of elastic material 45 is in the configuration illustrated in FIG. 11A. However, when axially compressed from its ends as illustrated in FIG. 11B, the slits 45s widen and the portions of the elastic material 45 between the slits 45s extend radially outward. Referring again to FIG. 12, the each end of the a tube of elastic material 45 is adhered to the flexible elongate member 20 using an adhesive suitable for this purpose such as those discussed above (e.g., a UV curable adhesive, a heat curable adhesive, an air curable adhesive, and so forth). The portions of the elastic material 45 between the slits 45s remain unattached to the member 20, but are provided with adhesive regions 46 on their top surfaces, which are also formed from a suitable adhesive material such as those discussed above (e.g., a UV curable adhesive). The assembly of FIG. 11A is then inserted into a balloon 120, and the inside wall of the balloon 120 pressed down against the adhesive regions 46, which are then cured (or given time to cure).

Figure 13A:
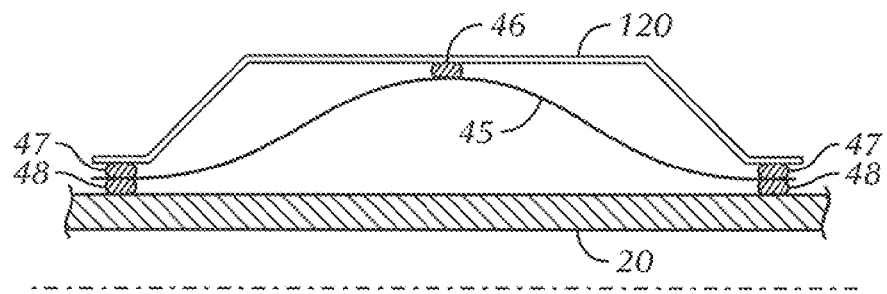
FIG. 13A is a schematic partial cross-sectional view illustrating an embodiment of a balloon catheter in accordance with the present invention which is formed using the assembly of FIG. 12.

As shown schematically in FIG. 13A, upon inflation of the balloon 120, the portions of the elastic material 45 between the slits pull away from the member 20. Being elastic, the material 45 exerts a radially inward force on the balloon, which can help maintain the structural integrity of the balloon 120 during high pressure inflation, and can also enhanced deflation of the balloon 120 due to the elastic rebound of the material 45. The ends of the balloon 120 are adhered to the end of the tube of elastic material 45 via adhesive regions 47 as illustrated in FIG. 13A. Also illustrated are the adhesive regions 48 whereby the tube of elastic material 45 is attached to member 20.

Figure 13B:
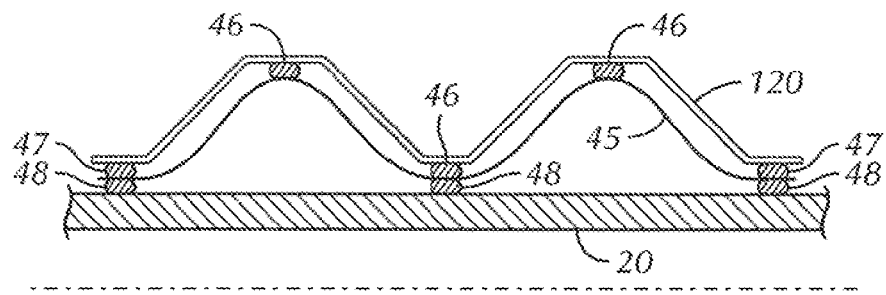
FIG. 13B is a schematic partial cross-sectional view illustrating an alternative embodiment to that of FIG. 13A.

Although a single "lobe" of elastic material 45 is provided in the cross section illustrated in FIG. 13A, multiple lobes could also be created. For example, as illustrated in FIG. 13B, an additional lobe may be created by providing an additional adhesive region 48, whereby the tube of elastic material 45 is attached to member 20 at an additional point, and by providing an additional adhesive region 46, wherein by the elastic material 45 is attached to the inner surface of the balloon 120 at an additional point.

Figure 14:
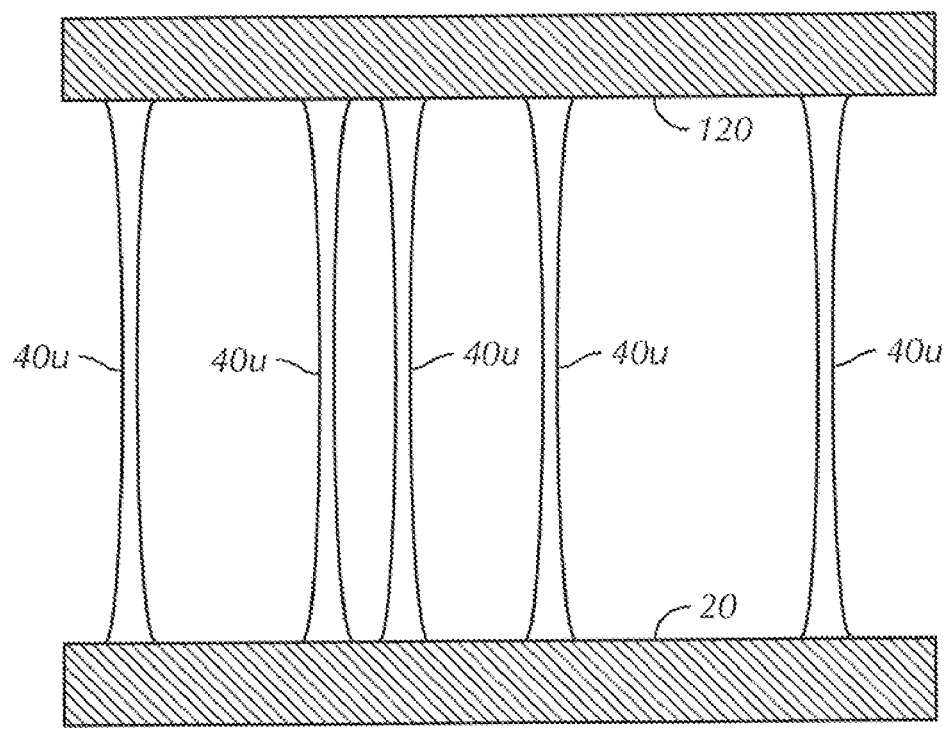
FIG. 14 is a schematic partial cross-sectional view illustrating an embodiment of the present invention in which cured adhesive fibers are disposed between the outer surface of a flexible elongate member and the inner surface of a balloon.

In still other embodiments, an assembly is formed in which a flexible elongate member is disposed within a balloon. An adhesive material is provided on the outer surface of the flexible elongate member, on the inner surface of the balloon, or both. The inner surface of the balloon is then brought into contact with the outer surface of the flexible elongate member, for example, by squeezing the balloon onto the flexible elongate member or by evacuating the balloon under negative pressure. Then, the balloon is expanded, for example, due to elastic rebound of the balloon material or by providing a negative pressure within the balloon. By selecting an adhesive material with the proper characteristics, a number of uncured strands of adhesive material 40u are formed between the inner surface of the balloon 120 and the outer surface of the flexible elongate member 20 as shown in the partial schematic illustration of FIG. 14. Suitable adhesives include those set forth above, such as urethane and ester adhesives. The adhesive is then allowed to passively cure or it is cured using active techniques such as those described above, resulting in the formation of reinforcing strands.

Figure 5A:
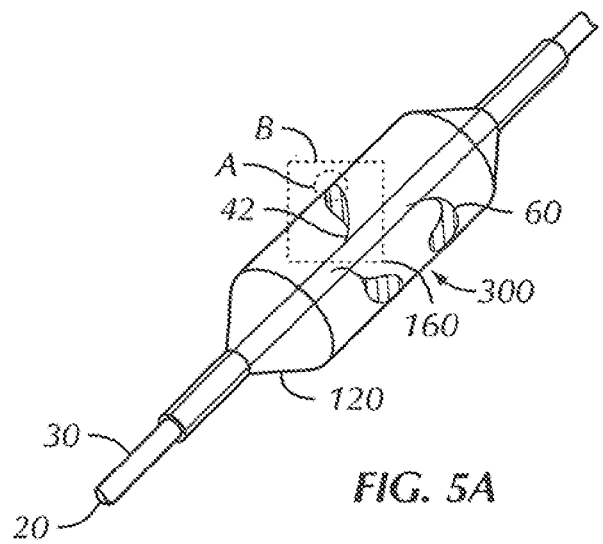
FIGS. 5A-5C are schematic illustrations of reinforced balloon catheters that also release a therapeutic agent upon inflation of the balloon.
Figure 5B:
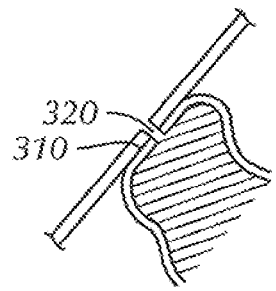
Figure 5C:
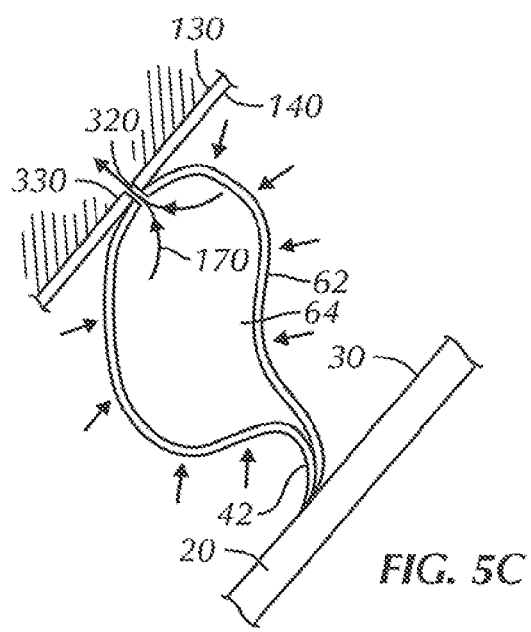

FIGS. 5A-5C are schematic illustrations of another embodiment of the present invention, wherein the strands comprise a hollow member such as a hollow tube or a flexible sac that is capable of holding and releasing a therapeutic agent. Thus, in lieu of, or in addition to, serving a structural reinforcing purpose, the applicants have discovered that strands may be utilized to provide a means for delivery of drugs to a biological site where the balloon catheter is employed, such as a vascular wall.

FIG. 5A is a see-through view of one embodiment of a drug-eluting balloon catheter 300 comprising an inflatable balloon 120 and an elongate member 20 as described above. The drug-eluting balloon catheter 300 further comprises a drug-releasing member, preferably a hollow member 60 such as a hollow tube, pocket, or sac, disposed in the annular lumen 160. FIG. 5B provides a close-up of Detail A of the catheter assembly of FIG. 5A, while FIG. 5C provides a close-up of Detail B of the catheter assembly of FIG. 5A. The longitudinal-sectional views of the catheter shown in FIGS. 5B and 5C, illustrate the release of the therapeutic agent from the sacs 60. As shown in FIGS. 5B and 5C, each hollow member 60 is defined by an exterior surface 62 and an interior cavity 64 containing a therapeutic agent 70. A portion of the exterior surface 62 is attached to the inner surface 140 of the balloon to form a contact interface 310 between the hollow member 60 and the balloon 120. As previously described, the drug-eluting balloon catheter may be produced by rotating the assembly around its longitudinal axis, resulting in radial attachment of the hollow members to the inner surface 140 of the balloon 120. Preferably, the hollow member 60 is comprised of a flexible material, for example, an elastomeric polymer, a metal or alloy foil, a liquid crystal polymer, or other polymeric materials as described above, particularly regarding the materials for the strands of the present invention.

In this embodiment, the drug-eluting balloon catheter 300 comprises a plurality of flexible sacs wherein each sac is defined by a head portion comprising the exterior surface 62, the interior cavity 64, and a tail portion 42 (e.g., a fiber or other strand material discussed above), wherein the tail portion 42 of each sac is attached to the outer surface of the elongate member 20. After the sacs 60 are attached to the inner surface of the balloon 120, a small channel such as a pore 320 can be drilled through the sac wall (e.g., though mechanical or laser drilling). Alternatively, the therapeutic agent may be placed within the sacs 60 after they are attached to the inner surface of the balloon 120. For example, an opening such as a pore 320 or other small channel can be made through the balloon wall and into the cavity 64 of the sac 60 and the therapeutic substance is inserted into the sac 60 through the opening. Preferably, as shown in FIGS. 5B and 5C, the pore 320 is disposed at the contact interface 310 and extends from the interior cavity 64 of the sac 60 to an outer surface 130 of the balloon 120, thereby allowing the therapeutic agent 170 contained in the interior cavity 64 of the hollow member to exit the device through the pore 320 upon inflation of the balloon 120. Inflation of the balloon 120 results in an increase in internal pressure within the balloon, which causes the therapeutic agent to be squeezed from the cavity 64, out of the balloon catheter 300, and onto/into an adjoining vessel wall 330.

In certain embodiments, a removable plug is placed within the pore 320 at the outer surface 130 of the balloon 120 such that the pore 320 is sealed from the external environment prior to inflation of the balloon catheter. The plug can be formed from a wide range of materials, for example, hydrophilic materials selected from the group consisting of biodegradable polymers, polysaccharides, hydrogels, and other materials that readily degrades or is readily dislodged from the pore 320 upon inflation of the balloon 120.

In certain other embodiments, the pore 320 at the outer surface 130 of the balloon 120 is provided with a pressure sensitive valve such as a poppet valve, such that the pore 320 is sealed from the external environment prior to inflation of the balloon catheter, and such that the pore 320 is opened upon inflation of the balloon 120.

A variety of therapeutic agents for treating a variety of diseases or conditions can be included within the catheters of the present invention, including but not limited to, therapeutic agents for treating restenosis. As used herein, "treatment"

refers to the prevention of a disease or condition, the reduction or elimination of symptoms associated with a disease or condition, or the substantial or complete elimination of a disease or condition. Preferred subjects are vertebrate subjects, more preferably mammalian subjects and more preferably human subjects.

For instance, numerous therapeutic agents have been identified as candidates for treatment of restenosis and include sirolimus, tacrolimus, everolimus, cyclosporine, natural and synthetic corticosteroids such as dexamethasone, M-prednisolone, leflunomide, mycophenolic acid, mizoribine, tranilast, biorest, estradiol, statins, paclitaxel, Epo D, actinomycin (e.g., actinomycin D), geldanamycin, cilostazole, methotrexate, angiopeptin, vincristine, mitomycin, QP-2, C-MYC antisense, ABT-578 (Abbott Laboratories), restenASE, choloro-deoxyadenosine, PCNA Ribozyme, batimastat, prolyl hydroxylase inhibitors, halofuginone, C-proteinase inhibitors, probucol, trapidil, liprostin, Resten-NG, Ap-17, abciximab, cladribine, clopidogrel and ridogrel, among others. Other appropriate therapeutic agents set forth in U.S. Patent Application Publication No. 2004/0106987, the entire disclosure of which is hereby incorporated by reference. The therapeutic agent may be in any form, including, but not limited to fluids such as including solutions, emulsions, particle dispersions, gels, and fluid particulates.

Figure 6A:
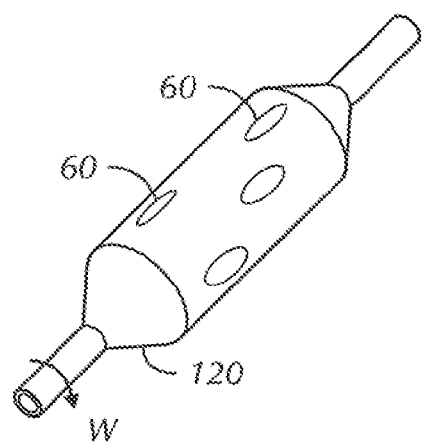
FIGS. 6A-6C are schematic illustrations of another embodiment of a drug-eluting balloon catheter in accordance with the invention.

FIG. 6A provides a see-through view of a drug-eluting balloon catheter according to another embodiment of the present invention, wherein hollow members such as sacs 60 containing a therapeutic agent are attached to the inner surface of the balloon 120, and are optionally also attached to an outer surface of an elongate member (not shown). In this embodiment, the hollow structures are adhered directly to the inner surface 140 of the balloon wall 132 (see FIG. 6B). Analogous to the procedure described above in FIGS. 5A-5C, therapeutic agent 170 may be inserted into the hollow members 60 prior to attachment tot the inner surface of the balloon 120 (followed by drilling a small hole, pore, or other channel), or by first drilling a small hole, pore, or other channel, and filling the hollow members 60. The pore 320 is sealed as discussed above.

Figure 6B:
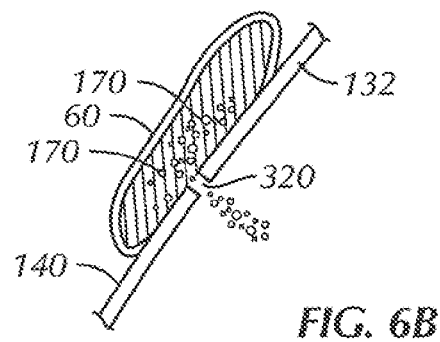

FIG. 6B schematically illustrates a longitudinal-sectional view of a portion of the catheter of FIG. 6A, and shows how the therapeutic agent 170 is released from the sac 60 via pore 320. Inflation of the balloon results in an increase in internal pressure within the sac 60 that causes the therapeutic agent to be squeezed out of the balloon catheter and, for example, into/onto an adjoining lumen wall (e.g., a vessel wall). The drug-releasing member of this embodiment comprises at least one hollow member 60 disposed at the inner surface 140 of the balloon wall 132, each hollow member 60 having an exterior surface and an interior cavity containing a therapeutic agent 170, wherein a portion of the exterior surface is attached to the inner surface 140 of the balloon wall 132 to form a contact interface between the hollow member and the balloon.

Figure 6C:
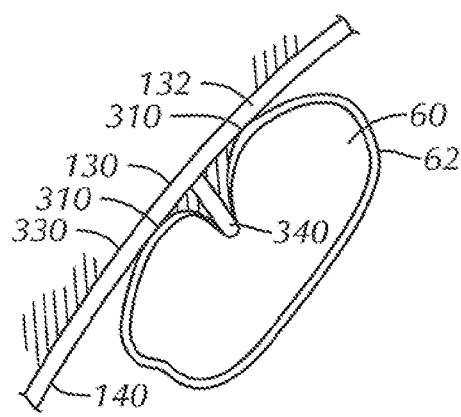

Referring now to FIG. 6C, in further embodiments, the drug-eluting catheter further comprises a piercing/puncturing member 340 disposed adjacent to the contact interface 310 and extending from the exterior surface 62 of the hollow member 60 to the an inner surface 140 of the balloon wall 132 such that upon inflation of the balloon within a vessel 330 or other body lumen, the increase in internal pressure within the balloon causes the puncturing/piercing member 340 to pierce the wall 132 of the balloon and the therapeutic agent contained in the interior cavity of the hollow member 60 is able to exit the device at the vessel wall 330, for example, through the use of a hollow puncturing/piercing member 340. The piercing/puncturing member 340 may comprise a lancet, a microneedle, a small blade, or any other mechanism for puncturing or cutting through the wall 132 of the balloon. In FIG. 6C, a hollow needle 340 is illustrated as the piercing/puncturing member. For example, a hole can be drilled in the balloon wall and a hollow needle 340 positioned within the hole in the balloon wall using an adhesive, such that it protrudes into the inner volume of the balloon.

To attach hollow members to the inner surface of the balloon, one can take a rod with a slotted middle section that can be inserted through the distal or proximal balloon opening. Pushing the rod on both ends inward will unfold he slotted middle section (analogous to the hollow tube of FIG. 11B above), bringing the middle section in contact with the balloon wall. The hollow members are mounted loosely on the outside of the middle strips (e.g., using gelatin) and a small drop of adhesive (e.g., UV glue) is provided at their outside surfaces. Upon the unfolding of the slotted middle section, which brings the hollow members into contact with the interior wall of the balloon, and upon subsequent curing of the adhesive (e.g., by exposure to UV light), the hollow members become attached to the inside of the balloon.

Figure 7:
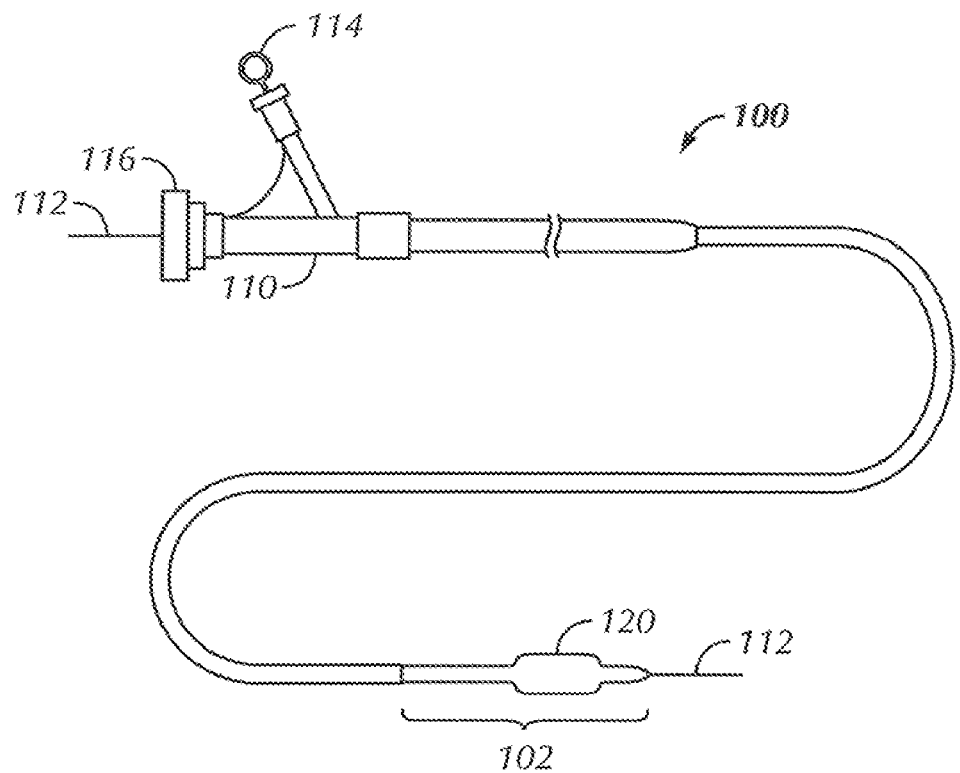
FIG. 7 is an external view of a balloon catheter of the present invention as part of a catheter system including a Luer assembly and a guide wire.

FIG. 7 is an exterior view of a typical balloon catheter 100 assembly incorporating various aspects of this invention. As described above, this invention generally relates to balloon catheters, which typically comprise the distal portion 102 of a balloon catheter assembly 100 such as the one illustrated in FIG. 7. The distal portion 102 may be of any desired length. Catheter assembly 100 is shown for the purpose of aiding in the understanding of the present invention and does not constitute the only assembly covered by this invention and any manner of balloon catheter assembly incorporating the aspects of this invention is within the scope thereof. In any event, catheter assembly 100 shown includes a Luer assembly 110 having a Luer port 114 for liquid introduction and a hub 116 for guide-wire 112 introduction and manipulation into the balloon 120. The Luer assembly 110 allows for access to the catheter lumen, such as the injection of inflation fluids or drugs, or the introduction of a guide wire 112.

In a typical blow molding process, a parison (i.e., an extruded hollow tube of molten polymer) is expanded within a mold to form a balloon. In certain aspects of the present invention, however, a parison is provided which has a different configuration. In particular, a parison is provided which contains polymeric material that bridges the outer tubular walls of the parison. This polymeric material can be different from or similar to the material used in the tubular wall, for example, using a co-extrusion process. Upon inflation of the balloon in the mold, these material bridges become reinforcement structures. In contrast to the techniques described hereinabove, in these aspects of the present invention, material is provided attached to the interior of the parison before the balloon is blown, so the reinforcement structures are co-formed with the balloon.

Figure 15:
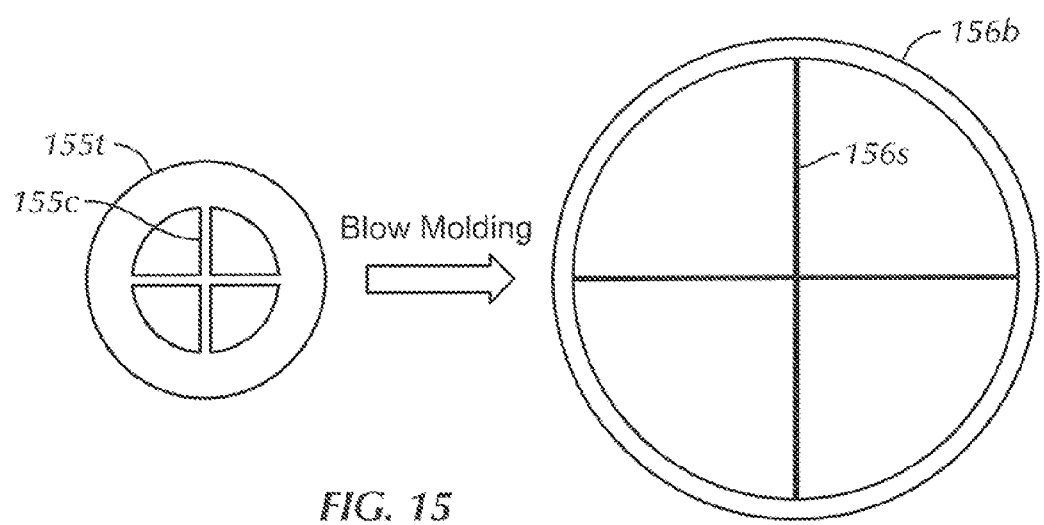
FIGS. 15 and 16 are schematic cross-sectional views illustrating two embodiments of the present invention in which an extruded parison is blow molded into a balloon having internal support structures.

Specific examples of these aspects of the invention will now be described in connection with FIGS. 15, 16 and 17A-B. Referring now to FIG. 15, a cross-section of a parison is illustrated which has a circular extrusion that forms a tubular outer region 155t, which is typical for parisons in balloon forming processes. However the parison illustrated also has an internal cross-shaped extrusion 155c, which takes the form of two intersecting plates that bridge opposite walls of the tubular outer region 15t. To make the initial shape of the parison, one could start, for example, with a tip and die combination that creates this kind of extrusion, rather than the tube shape that is normally used for parisons. During the blow molding process, the parison is stretched to form a balloon 156b having internal support structures 156s.

Figure 16:
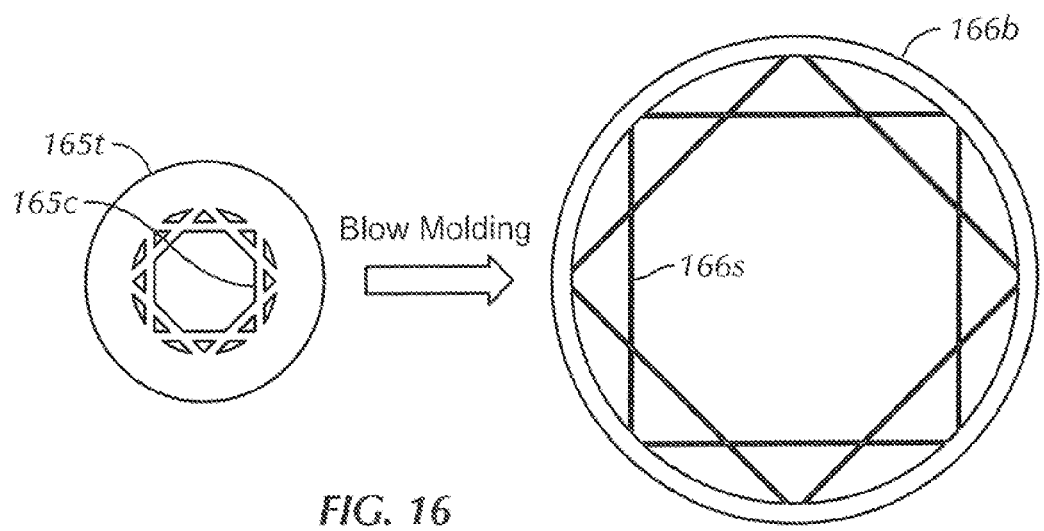

A structure similar to FIG. 15 is illustrated in FIG. 16. In FIG. 15, however, the reinforced balloon is formed from a parison having an outer tubular extrusion 155t and an internal cross-shaped extrusion 155c consisting of two intersecting plates, whereas the reinforced balloon in FIG. 16 is more complex, being formed from a parison having an outer tubular extrusion 165t and an internal extrusion 165c consisting of eight intersecting plates. Unlike the support structures 156s or the balloon 156b of FIG. 15, the support structures 166s of the balloon 166b of FIG. 16 do not occupy the cross-sectional center of the balloon 166b, allowing an inner elongate member (not shown) to be readily inserted and centered within the balloon 166b.

Using processes such as those illustrated in FIGS. 15 and 16, one can define precisely where the internal support structures are connected to the interior surface of the balloon. Besides providing reinforcement, such support structures can also assist in refolding the balloon in a predefined fashion.

Figure 17A:
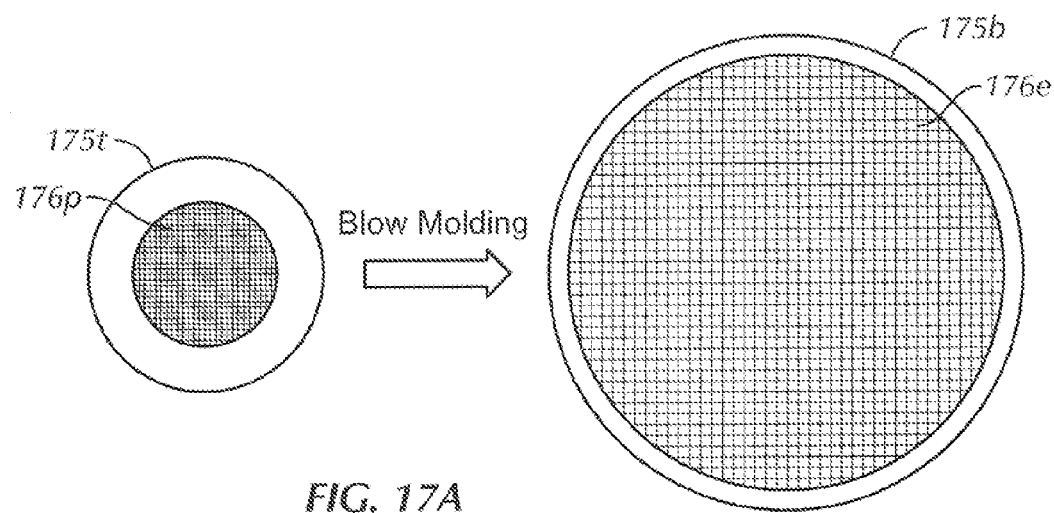
FIGS. 17A and 17B are schematic cross-sectional and longitudinal-sectional views illustrating an embodiments of the present invention in which an extruded parison with an internal porous material is blow molded into a balloon having a fibrous internal support network.
Figure 17B:
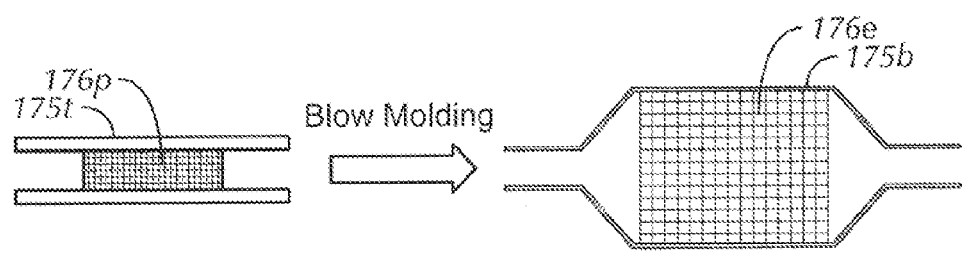

Yet another embodiment of the invention is illustrated in FIGS. 17A-B. Referring now to these figures, as in FIGS. 15 and 16 above, a parison is illustrated which has a circular extrusion in the form of tubular outer region 175t. However, unlike FIGS. 15 and 16 above, an elastic material (or an uncured precursor to an elastic material) having interconnected pores 176p is provided within the elastic material tubular outer region 175t, for example by injection. Although the entire interior of the tubular outer region 175t is filled with the material 176p as illustrated, one could also inject the material 176p only at specific positions in the parison (e.g., at specific axial positions), if desired. For the material 176p, a UV curable material 176p could be selected, for example, which would be cured after blowing using UV radiation. The interconnected porosity of the material 176p allows the pressurizing media to reach all points of the inner surface of the tubular outer region 175t, causing it to blow out into the form of a balloon 175b as normal. The pressurizing medial also results in the expansion of the material 176p, for example, such that a very open fibrous network 176e is formed within the balloon 175b, which can be subsequently allowed to cool (e.g., if a thermoplastic material), allowed to cure (e.g., if a passively curable material), or actively cured (e.g., if UV curable). Once a balloon is formed in this fashion, an inner elongate member (not shown) can be readily inserted within the balloon 175b, for example, by feeding a needle before pushing it though the fibrous network 176e.

Although various embodiments are specifically illustrated and described herein, it will be appreciated that modifications and variations of the present invention are covered by the above teachings and are within the purview of the appended claims without departing from the spirit and intended scope of the present invention. Furthermore, these examples should not be interpreted to limit the modifications and variations of the present invention covered by the claims but are merely illustrative of possible variations.

What is claimed is:

1. A therapeutic medical article comprising:
   an inflatable balloon having an inner surface that defines an inner volume;
   an elongate member having an outer surface, the elongate member being disposed within the inner volume of the inflatable balloon such that a lumen is established between the inner surface of the balloon and the outer surface of the elongate member when the balloon is in a non-collapsed state; and
   a plurality of flexible hollow members disposed in said lumen, each hollow member comprising an exterior surface and an interior cavity containing a therapeutic agent that serves as a reservoir for the therapeutic agent, wherein a portion of the exterior surface is attached to the inner surface of the balloon, and each hollow member having an associated channel that extends (a) from the outer surface of the balloon to the interior cavity of the hollow member or (b) from the outer surface of the balloon to a puncturing member, disposed between inner surface of the balloon and the exterior surface of the hollow member, which punctures the hollow member upon inflation of the balloon, such that, in either case, the therapeutic agent contained in the interior cavity of the hollow member is forced to exit the device through the channel when the balloon is inflated to working pressure.

2. The therapeutic medical article of claim 1, wherein the channel extends from the outer surface to the balloon to the interior cavity of the hollow member 3. The therapeutic medical article of claim 1, wherein the channel extends from the outer surface to the balloon to said puncturing member.

4. The therapeutic medical article of claim 1, wherein the hollow member is a flexible sac.

5. The therapeutic medical article of claim 1, wherein the hollow member comprises (a) a head portion comprising the exterior surface and the interior cavity and a (b) tail portion which is attached to the outer surface of the elongate member.

6. The therapeutic medical article of claim 1, wherein the therapeutic agent is in the form of a solution, particle dispersion, or gel.

7. The therapeutic medical article of claim 1, wherein the hollow member is a hollow fiber.

8. The therapeutic medical article of claim 1, wherein the channel is provided with a pressure sensitive valve.

9. The therapeutic medical article of claim 1, wherein the channel is blocked with a removable plug.

10. The therapeutic medical article of claim 9, wherein the plug comprises a hydrophilic material selected from the group consisting of biodegradable polymers, polysaccharides and hydrogels.

11. A therapeutic medical article comprising:
    an inflatable balloon having an inner surface that defines an inner volume;
    an elongate member having an outer surface, the elongate member being disposed within the inner volume of the inflatable balloon such that a lumen is established between the inner surface of the balloon and the outer surface of the elongate member when the balloon is in a non-collapsed state; and
    a plurality of flexible hollow members disposed in said lumen, each hollow member comprising an exterior surface and an interior cavity containing a therapeutic agent that serves as a source for the therapeutic agent, wherein a portion of the exterior surface is attached to the inner surface of the balloon, and each hollow member having an associated channel that extends a) from the outer surface of the balloon to the interior cavity of the hollow member or (b) from the outer surface of the balloon to a puncturing member, disposed between inner surface of the balloon and the exterior surface of the hollow member, which punctures the hollow member upon inflation of the balloon, such that, in either case. the therapeutic agent contained in the interior cavity of the hollow member is forced to exit the device through the channel when the balloon is inflated to working pressure, and wherein the hollow members comprise (a) a head portion comprising the exterior surface and the interior cavity and a (b) tail portion which comprises a strand material of solid cross section and which is attached to the outer surface of the elongate member.

12. The therapeutic article of claim 11 wherein said head portion comprises a hollow sac.

* * * * *

UNITED STATES PATENT AND TRADEMARK OFFICE
CERTIFICATE OF CORRECTION

PATENT NO. : 7,491,188 B2 Page 1 of 1
APPLICATION NO. : 10/963272
DATED : February 17, 2009
INVENTOR(S) : Thomas J. Holman et al.

It is certified that error appears in the above-identified patent and that said Letters Patent is hereby corrected as shown below:

Specification, Col. 2, line 31, after "the", change "inventing" to -- invention --.

Specification, Col. 2, line 33, after "having", delete "a".

Specification, Col. 4, line 58, after "an", change "embodiments" to -- embodiment --.

Specification, Col. 5, line 58, after "material", change "120" to -- 20 --.

Specification, Col. 7, line 35, after "For", delete "in".

Specification, Col. 7, line 35, before "where", change "case" to -- cases --.

Specification, Col. 10, line 49, before "tuned", change "fined" to -- fine --.

Specification, Col. 11, line 1, before "each", delete "the".

Specification, Col. 11, line 1, before "tube", delete "a".

Specification, Col. 11, line 19, after "also", change "enhanced" to -- enhance --.

Specification, Col. 12, line 31, after "e.g.," change "though" to -- through --.

Specification, Col. 13, line 24, after "fluids", delete "such as".

Specification, Col. 13, line 36, after "attachment", change "tot" to -- to --.

Specification, Col. 13, line 60, before "inner", delete "an".

Specification, Col. 14, line 12, after "unfold", change "he" to -- the --.

Signed and Sealed this

Twenty-first Day of April, 2009

JOHN DOLL
*Acting Director of the United States Patent and Trademark Office*